United States Patent [19]

Saito et al.

[11] Patent Number: 4,556,650

[45] Date of Patent: Dec. 3, 1985

[54] PHOSPHONIC ACID ESTERS AS PESTICIDES

[75] Inventors: Junichi Saito, Mitaka; Akio Kudamatsu, Kawasaki; Toyohiko Kume; Shinichi Tsuboi, both of Hino, all of Japan

[73] Assignee: Nihon Tokushu Noyaku Seizo K.K., Tokyo, Japan

[21] Appl. No.: 589,209

[22] Filed: Mar. 13, 1984

[30] Foreign Application Priority Data

Mar. 18, 1983 [JP] Japan ................... 58-44315

[51] Int. Cl.⁴ .......................... C07F 9/40; C07F 9/44; A01N 57/14; A01N 57/30
[52] U.S. Cl. ..................... 514/128; 260/949
[58] Field of Search ................. 260/949, 944; 514/128

[56] References Cited

U.S. PATENT DOCUMENTS 3,755,511  8/1973  McKendry et al. ............ 260/951

FOREIGN PATENT DOCUMENTS 0097270  1/1984  European Pat. Off. .
0119534  9/1984  European Pat. Off. .
1350718  11/1962  France .

*Primary Examiner*—Anton H. Sutto
*Attorney, Agent, or Firm*—Sprung Horn Kramer & Woods

[57] ABSTRACT

This invention relates to novel phosphonic acid esters represented by the following general formula (I)

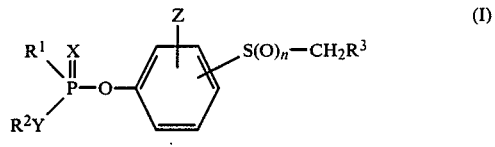

wherein
$R^1$ represents a lower alkyl group or an aryl group,
$R^2$ represents a lower alkyl group or a lower alkoxy-lower alkyl group,
$R^3$ represents a fluoro-substituted lower alkyl group,
X represents an oxygen or sulfur atom,
Y represents an oxygen or sulfur atom or a group of the formula

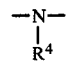

in which $R^4$ represents a hydrogen atom or a lower alkyl group,
Z represents a hydrogen atom, a halogen atom or a lower alkyl group, and
n represents 0 or 2,
which can be used as insecticidal, miticidal and nematocidal agents.

10 Claims, No Drawings

PHOSPHONIC ACID ESTERS AS PESTICIDES

This invention relates to novel phosphonic acid esters, processes for production thereof, and an insecticidal, miticidal and nematocidal agent.

More specifically, this invention relates to novel phosphonic acid esters represented by the following general formula (I).

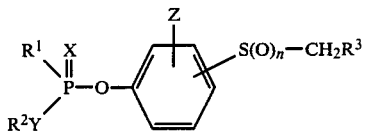
(I)

wherein $R^1$ represents a lower alkyl group or an aryl group,
$R^2$ represents a lower alkyl group or a lower alkoxy-lower alkyl group,
$R^3$ represents a fluoro-substituted lower alkyl group,
X represents an oxygen or sulfur atom,
Y represents an oxygen or sulfur atom or a group of the formula

in which $R^4$ represents a hydrogen atom or a lower alkyl group,
Z represents a hydrogen atom, a halogen atom or a lower alkyl group, and
n represents 0 or 2.

The compounds of general formula (I) can be produced by the following processes to which this invention also pertains.

Process (i)

A process for producing the phosphonic acid ester of general formula (I), which comprises reacting a compound represented by the general formula

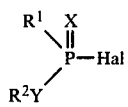
(II)

wherein $R^1$, $R^2$, X and Y are as defined and Hal represents a halogen atom,
with a compound represented by the general formula

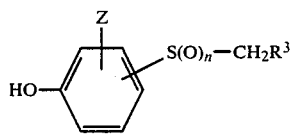
(III)

wherein $R^3$, Z and n are as defined,
in the presence of a base.

Process (ii)

A process for producing the phosphonic acid ester of general formula (I), which comprises reacting a compound represented by the general formula

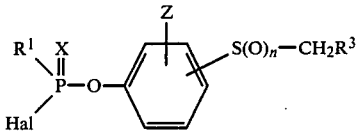
(IV)

wherein $R^1$, $R^3$, X, Z, n and Hal are as defined,
with a compound represented by the general formula $H-Y-R^2$ wherein $R^2$ and Y are as defined,
in the presence of a base.

Compounds of general formula (I) in which n is 2 can also be produced by the following process.

Process (iii)

A process for producing a phosphonic acid ester represented by the general formula

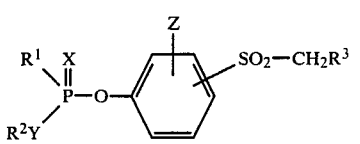
(I-b)

wherein $R^1$, $R^2$, $R^3$, X, Y and Z are the same as defined hereinabove,
which comprises reacting a phosphonic acid ester represented by the general formula

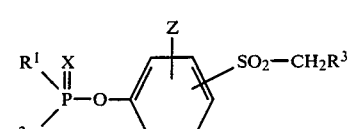
(I-a)

wherein $R^1$, $R^2$, $R^3$, X, Y and Z are as defined,
with a peroxide.

This invention also relates to an insecticidal, miticidal and nematocidal agent comprising the phosphonic acid ester of general formula (I) as an active ingredient.

U.S. Pat. No. 4,139,615 (corresponding to Japanese Laid-Open Patent Publication No. 151151/1977), a publication known before the filing of the present application, states to the effect that compounds of the general formula

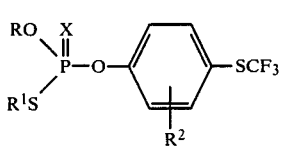
(A)

wherein R and $R^1$ are alkyl, $R^2$ is hydrogen or alkyl, and X is oxygen or sulfur,
have insecticidal, miticidal and nematocidal activities.

The present inventors have extensively studied derivatives of organophosphates which are typical insecticidal compounds, and consequently found that the phosphonic acid esters of general formula (I) which are not described in the known literature and are quite novel can be synthesized and that the compounds of formula (I) have unexpectedly excellent biological activities.

Investigations of the present inventors showed the result that the active compounds of formula (I) exhibit a very good control effect against noxious insects, mites and nematodes in agriculture, forestry and horticulture, and have technically excellent pesticidal activities which can never be attained by those compounds described in the above-cited known publication which seem to be structurally similar to the compounds of this invention.

It is an object of this invention therefore to provide the novel phosphonic acid esters of general formula (I), processes for production thereof, and their use as insecticidal, miticidal and nematocidal agents.

The above and other objects and advantages of this invention will become more apparent from the following description.

The active compounds of this invention exhibit an accurate control effect against noxious insects, mites and nematodes without causing phytotoxicity to cultivated plants. The compounds of this invention can be applied to the control and eradication of a wide range of pests, noxious sucking and biting insects, other plant parasites, pests on stored grains, and pests detrimental to hygiene.

Examples of such pests are shown below.

Examples of insects include coleopterous insects such as *Callosobruchus chinensis, Sitophilus zeamais, Tribolium castaneum, Epilachna vigintioctomaculata, Agriotes fuscicollis, Anomala rufocuprea, Leptinotarsa decemlineata,* Diabrotica spp., *Monochamus alternatus,* and *Lyctus brunneus;* lepidopterous insects such as *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Galleria mellonella* and *Phyllocnistis citrella;* hemipterous insects such as *Nephotettix cincticeps, Nilaparvata lugens, Pseudococcus comstocki, Unaspis yanonensis, Myzus persicae, Aphis pomi, Rhopalosiphum pseudobrassicas, Stephanitis nashi,* Nazara spp., *Cimex lectularius, Trialeurodes vaporariorum* and Psylla spp.; orthopterous insects such as *Blatella germanica, Periplaneta americana, Gryllotalpa africana* and *Locusta migratoria migratoriodes;* isopterous insects such as *Deucotermes speratus* and *Coptotermes formosanus;* and dipterous insects such as *Musca domestica, Aedes aegypti, Hylemia platura, Culex pipiens, Anopheles sinensis* and *Culex tritaeniorhynchus.*

Examples of mites are *Tetranychus telarius, Panonychus citri, Aculus pelekassi* and Torronomus spp.

Examples of the nematodes are *Meloidogyne incognita, Bursaphelenchus lignicolus* Mamiya et Kiyohara, *Aphelenchoides besseyi, Heterodera glycines* and Pratylenchus spp.

In the field of animal keeping and animal husbandry, the novel compounds of the invention can be effectively used against various animal parasites (endo- and ectoparasites), such as mites (including ticks), insects and worms. Examples of such animal parasites include such mites as Oranithodoros spp., Ixodes spp., and Boophilus spp., and such insects as Gastrophilus spp., Stomoxys spp., Trichodectes spp., Rhodnius spp., and Ctenocephalides canis.

In the present invention, substances which have a controlling effect against these pests are sometimes referred to generically as pesticides.

The compounds of general formula (I) in accordance with this invention can be produced, for example, by the following processes.

Process (i)

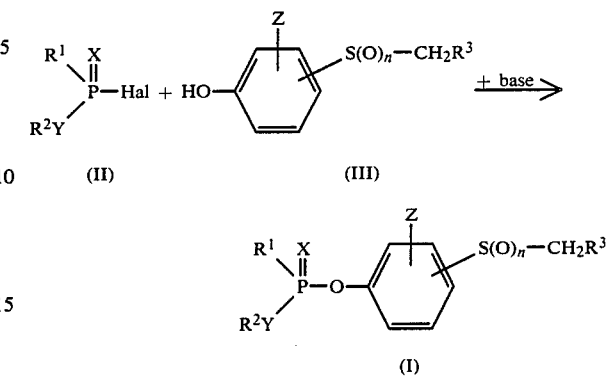

In the above formulae, $R^1$, $R^2$, $R^3$, X, Y, Z, n and Hal are as defined hereinabove.

In the above formulae, $R^1$ represents a lower alkyl group or an aryl group. Preferred examples of the lower alkyl group are those having 1 to 4 carbon atoms such as methyl, ethyl, propyl, isopropyl, and n-(iso-, sec-, or tert-) butyl. Particularly preferred are methyl and ethyl. Specific examples of the aryl group are phenyl, α-naphthyl and β-naphthyl, preferably aryl $R^1$ is phenyl.

$R^2$ represents a lower alkyl group or a lower alkoxy-lower alkyl group. Preferred examples of the lower alkyl are the same $C_1$–$C_4$ alkyl groups as exemplified above. Particularly preferred are methyl, ethyl, n- and i-propyl. Examples of the lower alkoxy-lower alkyl group are those which have the same lower alkyl groups as exemplified above and lower alkoxy groups with the same alkyl moiety as exemplified above, such as ethyloxyethyl.

$R^3$ represents a fluoro-substituted lower alkyl group. Preferred examples include fluoro-substituted $C_1$–$C_4$ alkyl groups with preferably 1 to 5 and particularly preferred 1 to 3 fluorine atoms, such as monofluoromethyl, difluoromethyl, trifluoromethyl, α,α,β,β-tetrafluoroethyl and pentafluoroethyl. The $CF_3$-group is particularly preferred as $R^3$. X represents an oxygen or sulfur atom, particularly preferably a sulfur atom.

Y represents an oxygen or sulfur atom or the group

in which $R^4$ represents a hydrogen atom or the same lower alkyl groups exemplified above under $R^1$, the methyl group being preferred as $R^4$.

Z represents a hydrogen atom, a halogen atom or a lower alkyl group. Specific examples of the halogen atom are fluoro, chloro, bromo, and iodo, preferably fluoro, chloro or bromo. The lower alkyl group is the same as exemplified hereinabove under $R^1$, such as the methyl group.

n represents 0 or 2 and preferably n represents 0.

Hal represents the same halogen atom as exemplified above. Hal represents preferably a chlorine or bromine atom and particularly preferably a chlorine atom.

Specific examples of the compound of general formula (II) used as a starting material in the process (i) for producing the compound of formula (I) shown schematically above are:
O-ethylmethanethiophosphonyl chloride,
O-ethylethanethiophosphonyl chloride,
O-ethylbenzenethiophosphonyl chloride,
N-methylmethanethiophosphonamide chloride,
N-isopropylmethanethiophosphonamide chloride,
N,N-dimethylmethanethiophosphonamide chloride,
S-propylmethanethiophosphonyl chloride,
S-propylmethanedithiophosphonyl chloride,
S-(2-ethoxyethyl)methanedithiophosphonyl chloride, and
O-ethylmethanephosphonyl chloride.

The corresponding bromides can also be cited as examples.

Specific examples of the compound of general formula (III) which is likewise a starting material include:
4-($\beta,\beta,\beta$-trifluoroethylthio)phenol,
3-methyl-4-($\beta,\beta,\beta$-trifluoroethylthio)phenol,
4-($\beta,\beta,\beta$-trifluoroethylsulfonyl)phenol,
2-($\beta,\beta,\beta$-trifluoroethylthio)phenol,
4-($\beta,\beta,\gamma,\gamma$-tetrafluoropropylthio)phenol,
2-($\beta,\beta,\gamma,\gamma$-tetrafluoropropylthio)phenol,
4-($\beta,\beta,\gamma,\gamma,\gamma$-pentafluoropropylthio)phenol, and
4-($\beta,\beta,\gamma,\gamma$-tetrafluoropropylsulfonyl)phenol.

Specific examples of the base used in the process (i) of this invention include inorganic bases such as sodium hydroxide, potassium hydroxide, potassium carbonate and sodium carbonate, and organic bases such as triethylamine, pyridine, N,N-dimethylaniline and isopropylamine.

By citing the following typical example, the above process will be described more specifically:

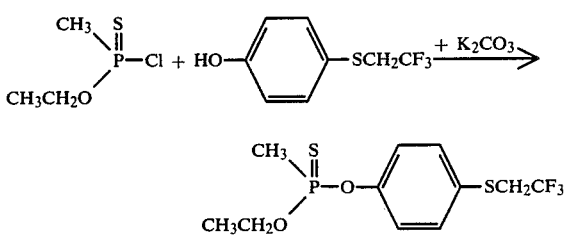

The process (i) for producing the active compound of this invention can be carried out desirably by using a solvent or diluent. For this purpose all inert solvents and diluents can be used.

Examples of such solvents or diluents include water; aliphatic, alicyclic and aromatic hydrocarbons (which may optionally be chlorinated) such as hexane, cyclohexane, petroleum ether, ligroin benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; tertiary alcohols such as tert-butyl alcohol; esters such as ethyl acetate and amyl acetate; acid amides such as dimethylformamide and dimethylacetamide; sulfones and sulfoxides such as dimethyl sulfoxide and sulfolane; and bases such as pyridine.

The reaction (i) in accordance with this invention may be carried out in the presence of an acid binder. Examples of the acid binder are hydroxides, carbonates and alcoholates of alkali metals, and tertiary amines (e.g., triethylamine, diethylaniline, dimethylaniline and pyridine) which are normally used.

The process (i) of this invention can be performed within a broad temperature range. For example, it can be carried out at a temperature between about 0° and about 150° C., preferably between about 10° and about 70° C. Desirably, the reaction is carried out under atmospheric pressure, but it is possible to operate under elevated or reduced pressure.

Process (ii)

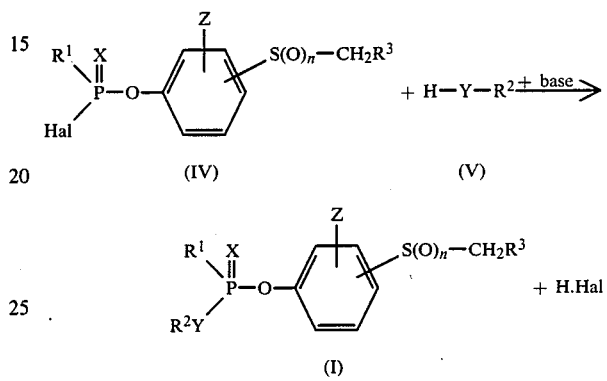

In the above formulae, $R^1$, $R^2$, $R^3$, X, Y, Z, n and Hal are the same as defined hereinabove.

In the above reaction scheme, examples of $R^1$, $R^2$, $R^3$, X, Y, Z, n and Hal may be the same as exemplified with regard to process (i).

Specific examples of the compound of general formula (IV) in the above reaction scheme include:
O-[4-($\beta,\beta,\beta$-trifluoroethylthio)phenyl]methanethiophosphonyl chloride,
O-[4-($\beta,\beta,\beta$-trifluoroethylthio)phenyl]ethanethiophosphonyl chloride,
O-[4-($\beta,\beta,\beta$-trifluoroethylthio)phenyl]benzenethiophosphonyl chloride,
O-[4-($\beta,\beta,\beta$-trifluoroethylthio)phenyl]methanephosphonyl chloride,
O-4-($\beta,\beta,\gamma,\gamma$-tetrafluoropropylsulfonyl)phenyl]methanethiophosphonyl chloride,
O-[2-($\beta,\beta,\beta$-trifluoroethylthio)phenyl]methanethiophosphonyl chloride,
O-[2-($\beta,\beta,\gamma,\gamma$-tetrafluoropropylthio)phenyl]methanethiophosphonyl chloride,
O-[4-($\beta,\beta,\beta$-trifluoroethylsulfonyl)phenyl]methanethiophosphonyl chloride,
O-[4-($\beta,\beta,\gamma,\gamma$-tetrafluoropropylthio)phenyl]methanethiophosphonyl chloride,
O-[4-($\beta,\beta,\gamma,\gamma,\gamma$-pentafluoropropylthio)phenyl]methanethiophosphonyl chloride, and
O-[3-methyl-4-($\beta,\beta,\beta$-trifluoroethylthio)phenyl]methanethiophosphonyl chloride.

The corresponding bromides may also be cited as examples.

Specific examples of the compound of general formula (V) which is likewise a starting material are ethyl alcohol, methyl alcohol, methylamine, isopropylamine, dimethylamine, propanethiol and 2-ethoxyethanethiol.

Examples of the base used in the above reaction may be the same as exemplified with regard to process (i).

By citing the following typical example, the above process will be specifically described.

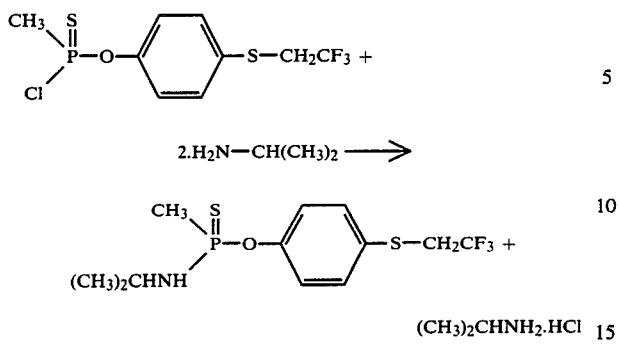

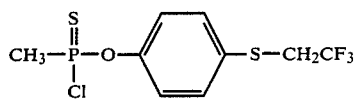

The above process for producing the compound of general formula (IV) can be carried out easily under the same conditions as in process (ii) above.

Compounds of general formula (I) in which n is 2 can also be produced by the following process.

Process (iii)

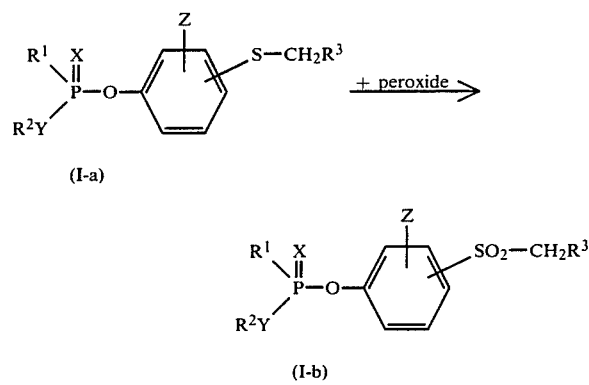

In the formulae, $R^1$, $R^2$, $R^3$, X, Y and Z are the same as defined hereinabove.

Examples of $R^1$, $R^2$, $R^3$, X, Y and Z in the above reaction scheme are the same as those given hereinabove.

The compounds of general formula (I-a) in the above reaction scheme are encompassed within the compounds of formula (I) in accordance with this invention. An example is O-ethyl O-[4-($\beta,\beta,\beta$-trifluoroethylthio)-phenyl]methanethiophosphonate.

Specific examples of the peroxide in the above reaction scheme are m-chloroperbenzoic acid and hydrogen peroxide.

The above process can be carried out over a broad temperature range using the same inert solvent or diluent as exemplified hereinabove. The reaction can be carried out generally at a temperature of about 0° to about 150° C., preferably about 10° to about 70° C. Desirably, the reaction is carried out under atmospheric pressure, but it is also possible to operate under elevated or reduced pressure.

The above process (ii) can be carried out over a broad temperature range in an inert solvent or diluent. Examples of the inert solvent or diluent are the same as given with regard to process (i) above and also include alcohols such as methanol, ethanol and isopropanol. The reaction can be carried out, for example, at a temperature between about 0° and about 150° C., preferably between about 10° and between about 70° C. Desirably, the reaction is carried out under atmospheric pressure, but it is also possible to operate under elevated or reduced pressure.

In process (ii) above, the compounds of general formula (IV) as a starting material can be produced, for example, by the following method:

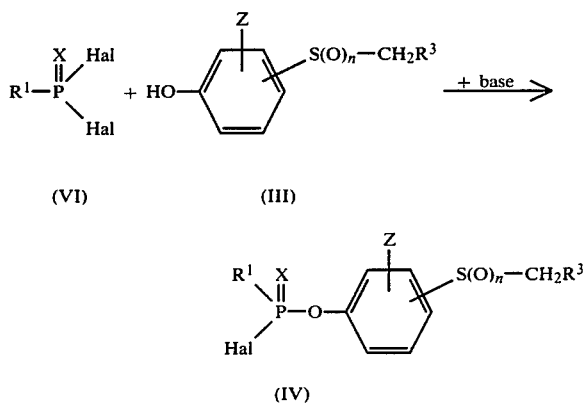

In the above formulae, $R^1$, $R^3$, X, Z, n and Hal are the same as defined hereinabove.

Specific examples of the compounds of general formula (VI) in the above reaction scheme are methanethiophosphonyl dichloride, ethanethiophosphonyl dichloride and benzenethiophosphonyl dichloride.

Specific examples of the compound of general formula (III) which is a starting material may be the same as exemplified with regard to process (i) above.

Specific examples of the base used in the above reaction are also the same as those given hereinabove.

By citing the following typical example, the above process will be specifically described:

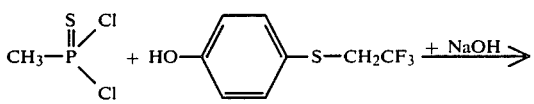

For use as an insecticidal, miticidal and nematocidal agent, the active compound of this invention may be diluted directly with water, or formulated into various forms using agriculturally acceptable adjuvants by methods generally practiced in the production of agricultural chemicals. In actual use, these various formulations may be applied directly or after diluting them with water to the desired concentrations.

Examples of the agriculturally acceptable adjuvants are diluents (solvents, extenders, carriers), surface-active agents (solubilizing agents, emulsifiers, dispersants, wetting agents), stabilizers, stickers, aerosol propellants and synergists.

Examples of the solvents are water, and organic solvents, for example hydrocarbons [e.g., n-hexane, petroleum ether, naphtha, petroleum fractions (e.g., paraffin waxes, kerosene, light oils, middle oils, and heavy oils), benzene, toluene and xylenes], halogenated hydrocarbons (e.g., methylene chloride, carbon tetrachloride, trichloroethylene, ethylene chloride, ethylene dibromide, chlorobenzene and chloroform), alcohols (e.g., methyl alcohol, ethyl alcohol, propyl alcohol, and ethylene glycol), ethers (e.g., ethyl ether, ethylene oxide and dioxane), alcohol ethers (e.g., ethylene glycol monomethyl ether), ketones (e.g., acetone and isophorone), esters (e.g., ethyl acetate and amyl acetate), amides (e.g., dimethylformamide and dimethylacetamide) and sulfoxides (e.g., dimethyl sulfoxide).

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (e.g., pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfuric acid esters (e.g., sodium laurylsulfate), arylsulfonic acids (e.g., alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (e.g., agricultural soaps, casein lime, sodium aliginate, polyvinyl alcohol, vinyl acetate-type adhesives and acrylic adhesives; aerosol propellants (e.g., trichlorofluoromethane, dichlorofluoromethane, 1,2,2-trichloro-1,1,2-trifluoroethane, chlorobenzene, LNG, and lower ethers); combustion controlling agents for fumigants (e.g., nitrite salts, zinc powder, dicyandiamide); oxygen yielding agents (e.g., chlorate salts, bichromate salts); toxicity reducing agents (e.g., zinc sulfate, ferrous chloride, copper sulfate); effect prolonging agents; dispersion stabilizers (e.g., casein, tragacanth, carboxymethyl cellulose (CMC) and polyvinyl alcohol (PVA); and synergists.

The compound of this invention can be formed into various formulations by methods generally practiced in the production of agricultural chemicals. Examples of the formulations are emulsifiable concentrates, oils, wettable powders, soluble powders, suspensions, dusts, granules, pulverulent compositions, fumigants, tablets, aerosols, pastes and capsules.

The insecticidal, miticidal and nematocidal agent of this invention may contain about 0.1 to about 95% by weight, preferably about 0.5 to about 90% by weight, of the aforesaid active ingredient.

In actual use, the suitable amount of the active compound in the aforesaid formulations and ready-to-use preparations is, for example, about 0.0001 to about 20% by weight, preferably about 0.005 to about 10% by weight.

The content of the active ingredient can be properly varied depending upon the type of the formulation, the method, purpose, time and locus of its application, the state of occurrence of pests to be controlled, etc.

If required, the compound of this invention may be used further in combination with other agricultural chemicals, for example other insecticides, fungicides, other miticides, other nematocides, antiviral agents, herbicides, plant growth regulators and attractants [e.g., organophosphate compounds, carbamate compounds, dithio(or thiol)carbamate compounds, organochlorine compounds, dinitro compounds, organosulfur or organometallic compounds, antibiotics, substituted diphenyl ether compounds, urea compounds, and triazine compounds], and/or fertilizers.

Various compositions and ready-to-use preparations containing the aforesaid active ingredient can be applied by various methods generally practiced in the field of agricultural chemical application, for example spraying (e.g., liquid spraying, misting, atomizing, dusting, granule scattering, water surface application, and pouring); fumigation; soil application (e.g., mixing, sprinkling, vaporizing pouring); surface application (e.g., coating, banding, dust coating, covering); and dipping. They can also be used by the so-called ultralow volume spraying method. According to this method, the active ingredient may be included in an amount of 95%.

The rate of application per unit area is, for example, about 0.03 to about 10 kg, preferably about 0.3 to about 6 kg, per hectare. In special cases, however, it may, and sometimes should, be outside the specified range.

According to this invention, there can be provided an insecticidal, miticidal and nematocidal composition comprising the compound of general formula (I) as an active ingredient and a diluent (a solvent and/or an extender and/or a carrier) and/or a surface-active agent, and if further required, a stabilizer, a sticker, a synergist, etc.

This invention also provides a method for controlling insects, mites and nematodes, which comprises applying to insects, mites and nematodes and/or their habitat the compound of general formula (I) alone or in admixture with a diluent (a solvent and/or an extender and/or a carrier) and/or a surface-active agent and if further required, a stabilizer, a sticker, a synergist, etc.

The following examples illustrate the present invention specifically. It should be noted however that the invention is not limited to these specific examples alone.

EXAMPLE 1

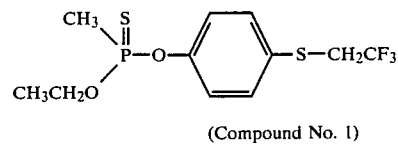

(Compound No. 1)

While a mixture consisting of 4.16 g of 4-($\beta,\beta,\beta$-trifluoroethylthio)phenol, 2.8 g of anhydrous potassium carbonate and 50 ml of methyl isobutyl ketone was stirred, 3.17 g of O-ethylmethanethiophosphonyl chloride was added dropwise to the mixture. During this time, the temperature of the reaction mixture was maintained at 20° to 30° C. After the mixture was stirred at 20° to 30° C. for 2 hours, the temperature of the mixture was raised to 55° to 60° C., and the mixture was further stirred for 4 hours. The reaction mixture was cooled to room temperature, washed with a 1% aqueous solution of sodium hydroxide and water in that order, and then dried over anhydrous sodium sulfate. The solvent and low-boiling substances were distilled off under reduced pressure to give 6.14 g of O-ethyl O-[4-($\beta,\beta,\beta$-trifluoroethylthio)phenyl]methanethiophosphonate. $n_D^{20} = 1.5210$.

EXAMPLE 2

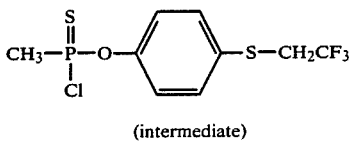

(intermediate)

A solution composed of 8.8 g of sodium hydroxide, 26 ml of water and 41.6 g of 4-($\beta,\beta,\beta$-trifluoroethylthio)phenol was added dropwise at 5° to 10° C. to 31.3 g of methanethiophosphonyl chloride which was being vigorously stirred. After the stirring was performed for 30 minutes, 300 ml of toluene was added, and the mixture was stirred for a while. The toluene layer was separated, washed with a cooled 1% aqueous solution of sodium hydroxide and ice water in this order, and then dried over calcium chloride. Toluene was distilled off, and the residue was distilled under reduced pressure to give 48 g of O-[4-($\beta,\beta,\beta$-trifluoroethylthio)phenyl]methanethiophosphonyl chloride. B.p. = 146°–148° C./0.7 mmHg.

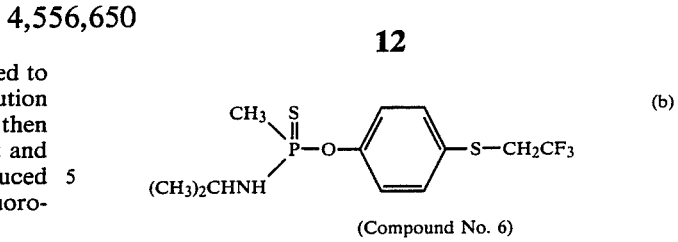

(Compound No. 6)

Isopropylamine (1.3 g) was added dropwise to 0° to 10° C. to a solution consisting of 3.2 g of O-[4-($\beta,\beta,\beta$-trifluoroethylthio)phenyl]methanethiophosphonyl chloride and 20 ml of toluene. The mixture was stirred for 3 hours at room temperature, and washed with 1% hydrochloric acid and water in that order. The toluene layer was dried over anhydrous sodium sulfate. Toluene was evaporated, and the residue was distilled under reduced pressure to give 1.8 g of N-isopropyl O-[4-($\beta,\beta,\beta$-trifluoroethylthio)phenyl]methanethiophosphonamide ester.

B.p.: 173°–176° C./0.6 mmHg.

$n_D^{20}$: 1.5368.

Compounds Nos. 2, 3, 4 and 5 were prepared in substantially the same way as in Example 1, and compounds Nos. 7, 8 and 9 were prepared in substantially the same way as in Example 2. The results are shown in Table 1.

TABLE 1/2

$$R^1\text{---}P(\text{=}X)(YR^2)\text{---}O\text{---}C_6H_3(Z)\text{---}S(O)_n\text{---}CH_2R^3$$

| Compound No. | $R^1$ | $R^2$ | $-S(O)_n-CH_2R^3$ | X | Y | Z | Physical constant $n_D^{20}$ |
|---|---|---|---|---|---|---|---|
| 2 | —CH₂CH₃ | —CH₂CH₃ | 4-S—CH₂CF₃ | S | O | H | 1.5180 |
| 3 | —C₆H₅ | —CH₂CH₃ | 4-S—CH₂CF₃ | S | O | H | 1.5573 |
| 4 | —CH₃ | —CH₂CH₃ | 4-S—CH₂CF₃ | S | O | 3-CH₃ | 1.5240 |
| 5 | —CH₃ | —CH₃ | 4-S—CH₂CF₃ | S | —NH | H | 1.5496 |
| 7 | —CH₃ | —CH₃ | 4-S—CH₂CF₃ | S | —N—CH₃ | H | 1.5402 |
| 8 | —CH₃ | —C₃H₇—n | 4-S—CH₂CF₃ | S | S | H | 1.5560 |
| 9 | —CH₃ | —C₂H₄OC₂H₅ | 4-S—CH₂CF₃ | S | S | H | 1.5454 |
| 10 | —CH₃ | —CH₂CH₃ | 4-S—CH₂CF₃ | O | O | H |  |
| 11 | —CH₃ | —CH₂Ch₃ | 2-S—CH₂CF₃ | S | O | H |  |
| 12 | —CH₃ | —CH₂CH₃ | 4-SO₂—CH₂Cf₃ | S | O | H |  |
| 13 | —CH₃ | —CH₂CH₃ | 4-S—CH₂—CF₂—CHF₂ | S | O | H |  |
| 14 | —CH₃ | —CH₂CH₃ | 4-S—CH₂—CF₂—CF₃ | S | O | H |  |
| 15 | —CH₃ | —C₃H₇—n | 4-S—CH₂CF₃ | S | S | H |  |

EXAMPLE 3

Wettable powder

Fifteen parts of compound No. 1 of the invention, 80 parts of a 1:5 mixture of white carbon (fine powder of hydrous amorphous silicon dioxide) and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and sprayed onto insects, mites and nematodes and/or their habitat.

EXAMPLE 4

Emulsifiable concentrate

Thirty parts of compound No. 2 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto insects, mites and nematodes and/or their habitat.

EXAMPLE 5

Dust

Two parts of compound No. 3 of the invention and 98 parts of powdery clay are pulverized and mixed to form a dust. It is scattered over insects, mites and nematodes and/or their habitat.

EXAMPLE 6

Dust

Compound No. 4 of the invention (1.5 parts), 0.5 part of isopropyl hydrogen phosphate, and 98 parts of powdery clay are pulverized and mixed to form a dust. It is scattered over insects, mites and nematodes and/or their habitat.

EXAMPLE 7

Granules

Water (25 parts) is added to a mixture consisting of 10 parts of compound No. 5 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over insects, mites and nematodes and/or their habitat.

EXAMPLE 8

Granules

Ninety-five parts of clay mineral particles having a particle size distribution between 0.2 and 2 mm are put in a rotary mixer, and with rotation, 5 parts of compound No. 6 of the invention is sprayed onto the particles to wet them uniformly. The granules obtained are scattered over insects, mites and nematodes and/or their habitat.

EXAMPLE 9

Oil

Compound No. 7 of the invention (0.5 part) and 99.5 parts of kerosene are mixed with stirring to form an oil. It is sprayed onto insects, mites and nematodes and/or their habitat.

EXAMPLE 10

Test on *Callosobruchus chinensis*

Preparation of a test chemical

Solvent: 3 parts by weight of xylene
Emulsifier: 1 part by weight of polyoxyethylene alkylphenyl ether To form a preparation of a suitable active compound, 1 part by weight of the active compound was mixed with the aforesaid amount of the solvent containing the aforesaid amount of the emulsifier, and the mixture was diluted with water to a predetermined concentration.

Testing method

A filter paper was spread on a Petri dish having a diameter of 9 cm, and 1 ml of the water dilution of the active compound in a predetermined concentration was put in it. Twenty heads of *Callosobruchus chinensis* were released into the Petri dish, and the dish was placed in a chamber kept at 28° C. The number of dead insects was examined 24 hours later, and the kill ratio was calculated.

The results are shown in Table 3.

TABLE 3

| Compound No. | Concentration of the active ingredient (ppm) | Kill ratio (%) |
|---|---|---|
| 1 | 1 | 100 |
| 2 | 1 | 100 |
| 3 | 1 | 100 |
| 4 | 1 | 100 |
| Comparison A-1 | 10 | 60 |
| | 1 | 0 |

Note:
Comparison A-1

$$\begin{array}{c} CH_3CH_2O \\ \diagdown \\ CH_3CH_2CH_2S \end{array} \!\!\! \begin{array}{c} S \\ \| \\ P-O- \end{array} \!\!\! \diagup\!\!\!\!\diagdown \!\!\!\! -SCF_3$$

(Compound described in U.S. Pat. No. 4,139,615)

EXAMPLE 11

Test on housefly (*Musca domestica*)

A filter paper was spread on a Petri dish having a diameter of 9 cm, and 1 ml of a water dilution in a predetermined concentration of the active compound prepared as in Example 10 was put into it. Ten female housefly imagoes having resistance to commercial organophosphorus agents were released into the Petri dish, and the dish was placed in a chamber kept at 28° C. The number of dead insects was examined 24 hours later, and the kill ratio was calculated. The results are shown in Table 4.

TABLE 4

| Compound No. | Concentration of the active ingredient (ppm) | Kill ratio (%) |
|---|---|---|
| 1 | 10 | 100 |
| 2 | 10 | 100 |
| 4 | 10 | 100 |
| 8 | 10 | 100 |
| Comparison A-1 | 100 | 0 |

Note:
Comparison A-1 is the same as in Table 3.

EXAMPLE 12

Test on *Tetranychus telarius*

Fifty to one hundred imagoes of *Tetranychus telarius* having resistance to organophosphorus agents were inoculated to the leaves of garden pea in the stage where two main leaves developed, which was cultivated in pots having a diameter of 6 cm. Two days later, a water dilution in a predetermined concentration of the active compound prepared as in Example 10 was sprayed at a rate of 40 ml per pot. The pots were placed in a greenhouse, and the control effect was evaluated 10 days later by the following control indices.

3: The number of surviving imagoes was 0%.
2: The number of surviving imagoes was more than 0% but less than 5% of that in a non-treated area.
1: The number of surviving imagoes was 5 to 50% of that in the non-treated area.
o: The number of surviving imagoes exceeded 50% of that in the non-treated area.

The results are shown in Table 5.

TABLE 5

| Compound No. | Concentration of the active ingredient (ppm) | Control index |
| --- | --- | --- |
| 1 | 100 | 3 |
| 2 | 100 | 3 |
| 9 | 100 | 3 |
| Comparison A-1 | 100 | 0 |

EXAMPLE 13

Test on German cockroach (*Blatella germanica*)

Testing method

A filter paper was spread on a Petri dish having a diameter of 9 cm, and 1 ml of a water dilution in a predetermined concentration of the active compound prepared as in Example 10 was put into it. Ten imagoes of German cockroach were released into the Petri dish, and the Petri dish was placed in a chamber kept at 28° C. Twenty four hours later, the number of dead insects was examined, and the kill ratio was calculated.

The results are shown in Table 6.

TABLE 6

| Compound No. | Concentration of the active ingredient (ppm) | Kill ratio (%) |
| --- | --- | --- |
| 1 | 10 | 100 |
| 2 | 10 | 100 |
| 3 | 100 | 100 |
| 4 | 10 | 100 |
| 6 | 100 | 100 |
| Compound A-1 | 100 | 10 |

Note:
Comparison A-1 was the same as in Table 3.

EXAMPLE 14

Test on larvae of *Culex pipiens*

Testing method

One hundred milliliters of a water dilution in a predetermined concentration of the active compound prepared as in Example 10 was placed in a tall Petri dish having a diameter of 9 cm, and 25 fourth-instar larvae of *Culex pipiens* were released into it, and the Petri dish was placed in a chamber kept at 28° C. The number of dead insects was examined 24 hours later and the kill ratio was calculated. The results are shown in Table 7.

TABLE 7

| Compound No. | Concentration of the active ingredient (ppm) | Kill ratio (%) |
| --- | --- | --- |
| 1 | 0.001 | 100 |
| 2 | 0.01 | 100 |
| 3 | 0.001 | 100 |
| 5 | 0.01 | 100 |
| 7 | 0.01 | 100 |

TABLE 7-continued

| Compound No. | Concentration of the active ingredient (ppm) | Kill ratio (%) |
| --- | --- | --- |
| Comparison A-1 | 0.1 | 70 |
| | 0.01 | 0 |

Note:
Comparison A-1 is the same as in Table 3.

EXAMPLE 15

Test on *Meloidogyne incognita*

Preparation of a test chemical

Two parts of the active compound and 98 parts of talc were pulverized and mixed.

Testing method

The test chemical prepared as above was added in a dosage of 25 and 10 ppm, respectively, to soil contaminated with *Meloidogyne incognita*. They were uniformly mixed with agitation, and the mixture was filled in pots (1/5000 are). Seeds of tomato (variety: Kurihara) were sown therein at a rate of about 20 per pot. The tomatoes were then cultivated in a greehouse. Four weeks later, the plants were pulled up with a care taken not to damage their roots. The degree of damage was examined on 10 of the pulled plants.

The results of the test show that the compounds of this invention, for example compounds Nos. 1, 4, 5, 6 and 7 produced a control effect of almost 100% when applied in 10 to 25 ppm as the concentration of the active ingredient.

The present invention described in detail hereinabove is summarized as follows:

(1) A phosphonic acid ester represented by the general formula

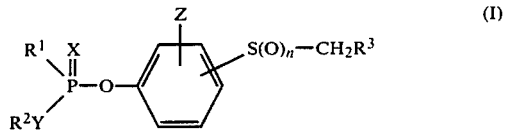

wherein $R^1$, $R^2$, $R^3$, X, Y, Z and n are as defined hereinabove.

(2) A process for producing the phosphonic acid ester of general formula (I), which comprises reacting a compound of the general formula

wherein $R^1$, $R^2$, X and Y are ad defined, and Hal represents a halogen atom,
with a compound represented by the general formula

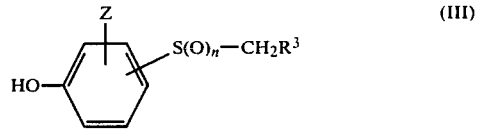

wherein $R^3$, Z and n are as defined above,
in the presence of a base.

(3) A process for producing the phosphonic acid ester of general formula (I), which comprises reacting a compound of the general formula

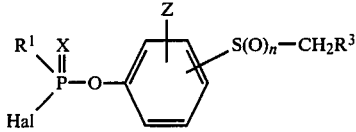

wherein $R^1$, $R^3$, X, Z, n and Hal are as defined above, with a compound of the general formula

wherein $R^2$ and Y are as defined above, in the presence of a base.

(4) A process for producing a phosphonic acid ester represented by the general formula

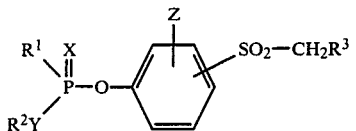

wherein $R^1$, $R^2$, $R^3$, X, Y and Z are as defined above, which comprises reacting a phosphonic acid represented by the general formula

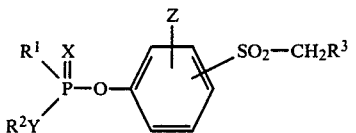

wherein $R^1$, $R^2$, $R^3$, X, Y and Z are as defined above, with a peroxide.

(5) An insecticidal, miticidal and nematocidal agent comprising the phosphonic acid ester of general formula (I) as an active ingredient.

(6) A method for controlling insects, mites and nematodes, which comprises applying the phosphonic acid ester of general formula (I) either alone or in combination with a diluent (a solvent and/or an extender and/or a carrier) and/or a surface-active agent and optionally a stabilizer, a sticker, and a synergist.

It will be appreciated that the instant specification and examples are set forth by way of illustration and not limitation, and that various modifications and changes may be made without departing from the spirit and scope of the present invention.

What is claimed is:

1. A phosphonic acid ester of the formula

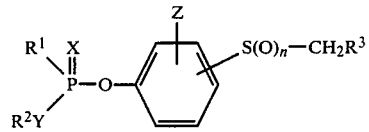

in which
$R^1$ is $C_{1-4}$-alkyl, phenyl or naphthyl,
$R^2$ is $C_{1-4}$-alkyl or $C_{1-4}$-alkoxy-$C_{1-4}$-alkyl,
$R^3$ is fluoro-substituted $C_{1-4}$-alkyl,
X is an oxygen or sulfur atom,
Y is an oxygen or sulfur atom or a group of the formula

in which $R^4$ is a hydrogen atom or $C_{1-4}$-alkyl, and
Z is a hydrogen atom, a halogen atom or $C_{1-4}$-alkyl, and
n is 0 or 2.

2. A method of combating insects, mites and nematodes which comprises applying to the insects, mites and nematodes or to a habitat thereof, an insecticidally, miticidally and nematicidally effective amount of a compound according to claim 1.

3. The method according to claim 2, wherein such compound is

O-ethyl O-[4-($\beta,\beta,\beta$-trifluoroethylthio)phenyl]methanethiophosphonate, O-ethyl O-[4-($\beta,\beta,\beta$-trifluoroethylthio)phenyl]ethanethiophosphonate, O-ethyl O-[4-$\beta,\beta,\beta$-trifluoroethylthio)phenyl]benzenethiophosphonate, N-isopropyl O-[4-($\beta,\beta,\beta$-trifluoroethylthio)phenyl]-methanethiophosphonamide ester or S-(2-ethoxyethyl) O-[4-($\beta,\beta,\beta$-trifluoroethylthio)-phenyl]-methane dithiophosphonate.

4. An insecticidal, miticidal and nematocidal composition comprising an insecticidally, miticidally and nematocidally effective amount of a phosphonic acid ester according to claim 1 in admixture with a diluent.

5. A compound according to claim 1, in which
$R^1$ is methyl, ethyl or phenyl,
$R^2$ is methyl, ethyl, n- or i-propyl, or ethyloxyethyl,
$R^3$ is mono-fluoromethyl, difluoromethyl, trifluoromethyl, $\alpha,\alpha,\beta,\beta$-tetrafluoroethyl or pentafluoroethyyl,
X is a sulfur atom,
Y is an oxygen or sulfur atom, —NH— or —NCH$_3$—,
Z is a hydrogen atom, a halogen atom or methyl, and
n is 0.

6. A compound according to claim 1, wherein such compound is O-ethyl O-[4-($\beta,\beta,\beta$-trifluoroethylthio)-phenyl]methanethiophosphonate of the formula

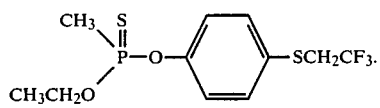

7. A compound according to claim 1, wherein such compound is O-ethyl O-[4-($\beta,\beta,\beta$-trifluoroethylthio)-phenyl]ethanethiophosphonate of the following formula

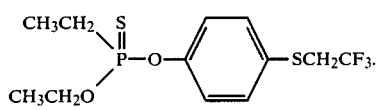

8. A compound according to claim 1, wherein such compound is O-ethyl O-[4-($\beta,\beta,\beta$-trifluoroethylthio)-phenyl]benzenethiophosphonate of the following formula

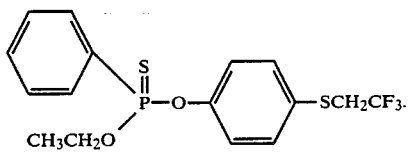
9. A compound according to claim 1, wherein such compound is N-isopropyl O-[4-(β,β,β-trifluoroethylthio)phenyl]methanethiophosphonamide ester of the following formula
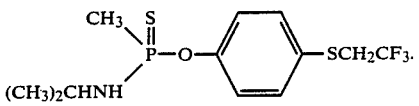
10. A compound according to claim 1, wherein such compound is S-(2-ethoxyethyl) O-[4-(β,β,β-trifluoroethylthio)phenyl]-methanedithiophosphonate of the following formula
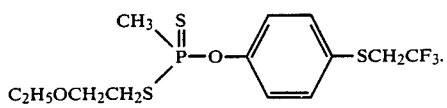
* * * * *

UNITED STATES PATENT AND TRADEMARK OFFICE
CERTIFICATE OF CORRECTION

PATENT NO. : 4,556,650

DATED : December 3, 1985

INVENTOR(S) : Junichi Saito et al.

It is certified that error appears in the above-identified patent and that said Letters Patent is hereby corrected as shown below:

Col. 4, line 54      Delete "groups" and substitute --group--

Col. 4, line 63      Delete "n" and substitute --$\underline{n}$--

Col. 9, lines 40, 41      Correct spelling of "alginate"

Col. 12, line 9      After "dropwise" delete "to" and substitute --at--

Col. 12, "Table 1/2", Compound 11, under "$R^2$"      Delete "$-CH_2Ch_3$" and substitute -- $-CH_2CH_3$ --

Col. 12, "Table 1/2", Compound 12 under 4th column      Delete "$4-SO_2-CH_2Cf_3$" and substitute -- $4-SO_2-CH_2CF_3$ --

Col. 17, line 33      Right side of structure delete "$SO_2-CH_2R^3$" and substitute --$S-CH_2R^3$--

Signed and Sealed this

Eleventh Day of March 1986

[SEAL]

Attest:

DONALD J. QUIGG

Attesting Officer      Commissioner of Patents and Trademarks